United States Patent [19]

Sasaki et al.

[11] Patent Number: 4,770,880

[45] Date of Patent: Sep. 13, 1988

[54] METHOD FOR PRODUCING FIBER-RICH VEGETABLE MATERIAL CAPABLE OF ADSORBING MUTAGEN AND PRODUCT

[76] Inventors: Yoshiteru Sasaki, Aza Nakayubetsuminamicho Kamiybetsusho, Monbetsu-gun, Hokkaido; Tsuneo Kada, 1111, Yata, Mishima-shi, Shizuoka-ken; Tatsuo Emura, 4-1-15, Toyohira 3-jo, Toyohira-ku, Sapporo-shi, Hokkaido, all of Japan

[21] Appl. No.: 756,801

[22] Filed: Jul. 19, 1985

[30] Foreign Application Priority Data

Jul. 31, 1984 [JP] Japan .................................. 59-162666

[51] Int. Cl.⁴ .............................................. A61K 35/78
[52] U.S. Cl. .................................. 424/195.1; 514/917
[58] Field of Search ....................... 424/195.1; 514/917

[56] References Cited

U.S. PATENT DOCUMENTS 4,147,779  4/1979  Naito et al. ...................... 424/195.1

OTHER PUBLICATIONS

Kada et al., Chem. Abst. 102:91223p, 1985.
Inoue et al., Chem. Abst. 94:186596t, 1981.
K. Morita et al., "Studies on Natural Desmutagens:-Screening for Vegetable and Fruit Factors Active in Activation of Mutagen Pyrolysis Products for Amino Acids," Agric. Biol. Chem. 42(6), 1235–1238, 1978.
T. Inoue et al., "Purification and Properties of a Plant Desmutagenic Factor for the Mutagenic Principle of Tryptophan Pyrolysate", Agric. Biol. Chem., 45(2), 345–353, 1981.
T. Kada et al., "Anti-Mutagenic Action of Vegetable Factor(s) on the Mutagenic Principle of Tryptophane Pyrolysate", Mutagen Research, 53(1978) 351–353.
Article: *Adsorption of Pyrolysate Mutagens by Vegetable Fibers*—Tsuneo Kada et al.-Mutation Research, vol. 141(1984), pp. 149–152.

*Primary Examiner*—J. Rollins
*Attorney, Agent, or Firm*—Sandler & Greenblum

[57] ABSTRACT

A method for producing a product capable of adsorbing mutagen involving providing a fiber-rich, vegetable material capable of adsorbing mutagen by separating fibers from a vegetable, boiling the fibers and then washing and dewatering the fibers, prior to treating the fibers to produce dehydrated, fiber-rich vegetable material in particulate form by subjecting the fiber-rich material to a dehydration technique which preferably involves co-drying the fibers with carrier materials, and an ingestible product including fiber-rich vegetable material made from cabbage, radish, bamboo sprout, onion, carrot, pimiento, spinach, soybean malt, and asparagus.

9 Claims, 3 Drawing Sheets

FIG. 1.

DL- TRYPTOPHAN IS CHARGED IN A FLASK
│
BURNED BY GAS BURNER
│
COOLED TO OBTAIN TAR
│
EXTRACTED WITH ETHER
│
ETHER EXTRACT
(BASIC FRACTION)
│
EVAPORATED
│
DISSOLVED IN ETHYL ACETATE
│
SUBJECTED TO SILICA GEL COLUMN CHROMATOGRAPHY

ETHYL ACETATE    30% METHANOL    MUTAGENIC ACTIVITY
                 IN ETHYL ACETATE    MEASURED IN EACH FRACTION

FRACTION SHOWING MUTAGENIC ACTIVITY (SINGLE PEAK)
│
SUBJECTED TO ALUMINA COLUMN CHROMATOGRAPHY ($Al_2O_3$)
│
30% METHANOL DISSOLVED IN ETHYL ACETATE
                    │ MUTAGENIC ACTIVITY WAS
                    │ MEASURED IN EACH FRACTION

POOLED MUTAGENIC FRACTION
│
CM-SEPHADEX C-25 COLUMN
│
METHANOL AND 2.0N ACETIC ACID (3:1, V/V)
                    │ SINGLE PEAK
                    │ MUTAGENIC ACTIVITY WAS
                    │ MEASURED IN EACH FRACTION

SINGLE PEAK
│
MUTAGENIC ACTIVITY FRACTION
│
SEPHADEX LH-20 COLUMN
│
METHANOL
│
TWO PEAKS WERE OBTAINED   HIGH MUTAGENIC ACTIVITY WAS MEASURED

ACETATE SALT                     PURIFIED BY CM-SEPHADEX
(CRYSTALLIZATION)                CHROMATOGRAPHY

NMR, SPECTROPHOTO-               CRYSTALLIZATION
METRIC ANALYSIS      ACTIVE      NMR, SPECTROPHOTO
                     SUBSTANCE       METRIC ANALYSIS

TRP-P-1                          TRP-P-2

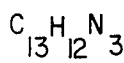  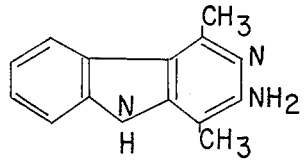    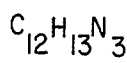  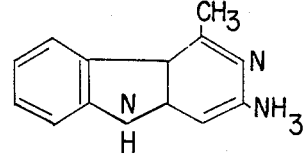

METHOD FOR PRODUCING FIBER-RICH VEGETABLE MATERIAL CAPABLE OF ADSORBING MUTAGEN AND PRODUCT

1. FIELD OF THE INVENTION

The present invention relates to a fiber-rich vegetable material, particularly fibers separated from asparagus, capable of adsorbing mutagen, a method of preparing the same, a method for using the same to adsorb mutagen, and a method for isolating mutagenic substances from organic material.

2. DISCUSSION OF BACKGROUND AND RELATED INFORMATION

Although it was first observed over thirty years ago that carcinogenic substances are mutagenic substances, only recently has a test been developed which is capable of proving this hypothesis. The Ames test, developed by Dr. Bruce Ames, has found that many chemical carcinogens or cancer-causing agents are potent frameshift mutagens or substances which may be metabolized in cells to forms that are frameshift mutagen. In brief, the Ames test is an assay for screening compounds for their ability to revert a series of known frameshift mutations in the hisD gene to wild type, which is readily assayed because wild-type mutated cells form colonies on medium that lack histidine. The rational of the test is based on the premise that mutagenesis and cancer induction both result from alteration of the DNA of a cell. Experimentally, over 90% of the carcinogens tested have been determined to be mutagens. The Ames test, as indicated above, measures the rate of reversion of histidine auxotrophs of Salmonella to prototrophy in both the presence and absence of the chemical being tested. If the chemical is mutagenic, it will increase the reversion rate. The test also gives some idea of how powerful a mutagen, or how potentially hazardous, a chemical is by a number of revertants that arise. The more powerful the mutagen, the greater number of revertants.

SUMMARY OF THE INVENTION

Notwithstanding the progress which has been made in identifying mutagenic substances, the list is by no means exhaustive. Considerable time and effort is required to conduct tests on an infinite number of materials in an effort to completely identify substances which are mutagens, and by implication, carcinogenic.

The present invention is based on the discovery that vegetable material may be processed so as to extract, isolate, or otherwise separate fibrous components having the capability of adsorbing mutagens. Resultant fibrous, mutagen-adsorbing vegetable material can be further processed, for example into a dehydrated powder, which may be incorporated with other edible materials to be used as a food supplement for ingestion with other foodstuffs which may contain mutagenic substances.

An object of the present invention is to provide a method for producing a product capable of adsorbing mutagen by first providing a fiber-rich vegetable material capable of adsorbing mutagen, followed by treating the fiber-rich vegetable material to produce a dehydrated, fiber-rich vegetable material in particulate form.

Another object of the present invention is a method for producing a product capable of adsorbing mutagen which involves separating fibers capable of adsorbing mutagen from a vegetable and boiling the separated fibers after which the fibers are preferably washed with water and dewatered prior to treating to result with a dehydrated, fiber-rich vegetable material in particulate form, as by dehydrating the separated fibers, preferably by co-drying the fibrous material or dry-blending dehydrated fibers with carrier materials which are preferably members selected from the group consisting of dehydrated fruit and vegetable particulate materials, such as starch and fruit powders, of which powdered pumpkin and plum are preferred.

A further object of the present invention is to provide a method for producing a product capable of adsorbing mutagens involving treating a fiber-rich vegetable material selected from the group consisting of cabbage, radish, bamboo sprout, onion, carrot, pimiento, spinach, soybean malt, cellulose and preferably asparagus to produce dehydrated, fiber-rich vegetable material particulates, preferably in the form of powder, granules, and agglomerates of powder and/or granules.

It is another object of the present invention to provide an ingestible product comprising fiber-rich vegetable material capable of adsorbing mutagen, wherein the vegetable material is preferably a member selected from the group consisting of cabbage, radish, bamboo sprout, onion, carrot, pimiento, spinach, soybean malt, cellulose, and most preferably asparagus, particularly in a dry state, such as powder, granules, and agglomerates of powder and/or granules.

It is a further object of the present invention to provide an ingestible product comprising fiber-rich dry, particulate asparagus material in combination with a carrier material such as dry fruit and vegetable particulate material which is preferably starch or fruit powder of which pumpkin and plum is preferred.

A still further object of the present invention is provide a method for adsorbing mutagen present in foodstuff by incorporating an amount of fiber-rich vegetable material capable of adsorbing mutagen with a foodstuff, wherein the fiber-rich vegetable material is a member selected from a group consisting of cabbage, radish, bamboo sprout, onion, pimiento, spinach, soybean malt, cellulose, and preferably asparagus, particularly in dry particulate form, such as powder, granules, and agglomerates of powder and/or granules, more preferably in combination of with a carrier material which may be selected from the group consisting of dehydrated fruit and vegetable particulate materials such as starch and fruit powders of which pumpkin and plum are preferred.

A yet still further object of the present invention is to provide a method for isolating mutagenic substances from organic materials by first providing organic material containing a source of mutagenic substance, heating the source of mutagenic substance to obtain tars of the source of mutagenic material, separating mutagenic substance from the tars, and forming crystals of the separated mutagenic substances, wherein the separation of mutagenic substance from tars involves subjecting the mutagenic substance to chromatography procedures which may be selected from the group consisting of silica gel column chromatography, alumina column chromatography, CM-Sephadex C-25 column chromatography, Sephadex LH-20 column chromatography, Yanafax LH-20 column chromatography, CM-Yakuatex chromatography, and wherein the formation of crystals is preferably accomplished by subjecting the mutagenic substance to an acetate salt crystallization procedure.

Yet another object of the present invention is to provide a method for isolating mutagenic substances from organic materials involving heating a source of mutagenic substance to obtain tars which are then cooled and treated with a first solvent, preferably ether, to extract mutagenic substance from the tars, collecting the basic fraction of solvent extract containing the mutagenic substance, subjecting the basic fraction of solvent extract to a procedure to remove the solvent from the mutagenic substance, and dissolving the mutagenic substance in a second solvent, preferably ethyl acetate, prior to subjecting the resulting solution containing the mutagenic substance to a chromatography procedure.

Yet another still further object of the present invention is to provide a method for isolating mutagenic substances from organic materials wherein the isolated mutagenic substance is identified, preferably by using NMR, UV Analysis.

BRIEF DESCRIPTION OF THE DRAWINGS

FIG. 1 illustrates a flow chart for a method for isolating tryptophan;

DETAILED DESCRIPTION OF PREFERRED EMBODIMENTS

Figure 2:
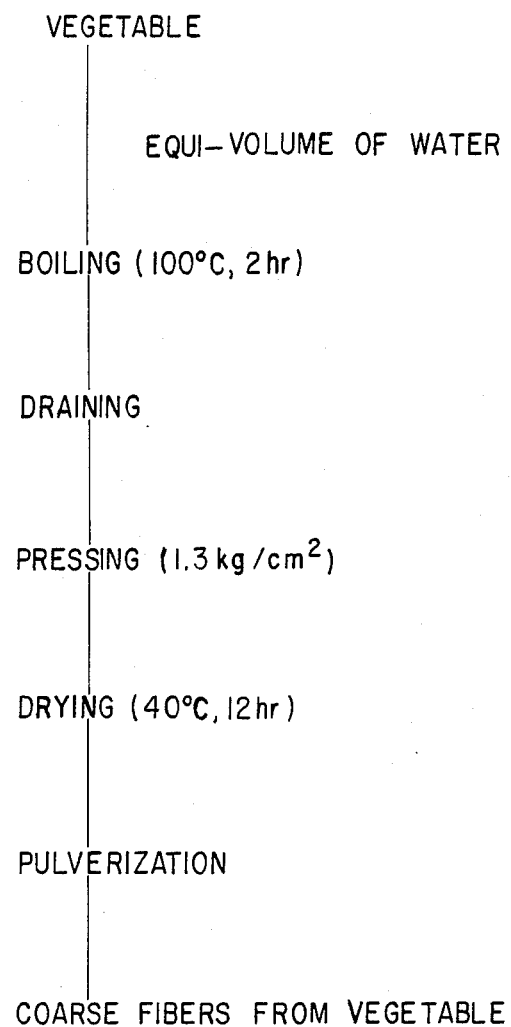
FIG. 2 illustrates a flow chart for an experimental procedure for determining mutagen adsorbility of edible plants.
Figure 3:
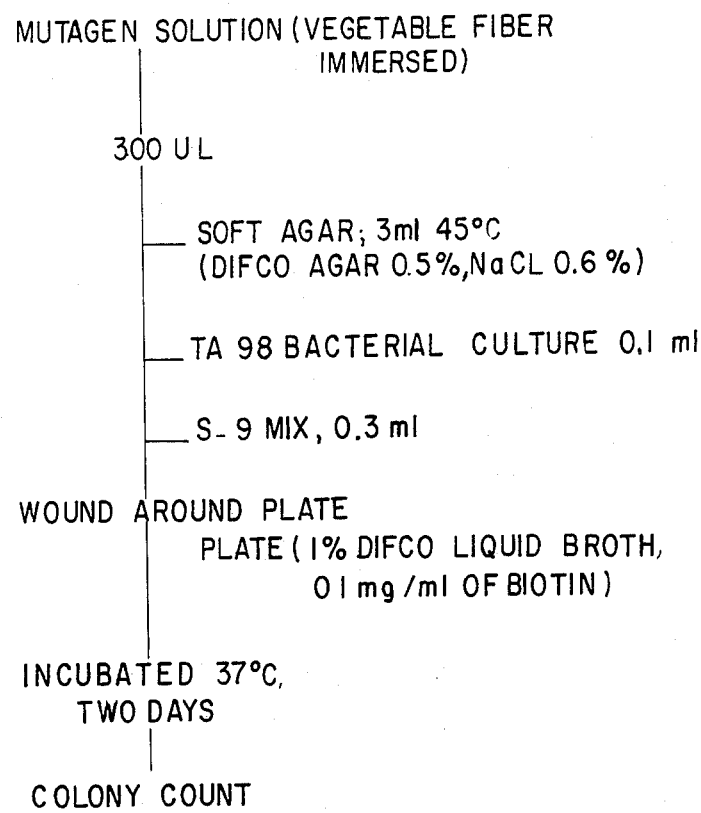
FIG. 3 illustrated a flow chart for the procedure to which vegetable fibers are subjected during tests to determine the adsorbility of tryptophan.

Mutagenic substances to which an individual may be exposed as a result of his environment, occur naturally as well as being synthetically produced. More specifically, mutagenic substances can be classified into three groups:

(I) synthesized chemical substances such as $AF_2$ Butter Yellow, vinyl chloride monomer or the like;

(II) substances resulting from heat treatment of proteins, amino acids, saccharides and similar macromolecular compounds; and (III) naturally occurring substances, such as mycotoxin and antibiotics produced from molds and actiomycetes or flavons and certain types of hydrazines contained in plant bodies.

The mutagenic substances of the second group produced through heat treatment are also resulted from tobacco tars or upon baking meats or fishes. Among the mutagenic substances thus produced, B(a)P (benz-(a)-pyrene) corresponds to only 1/1000–1/20000 of the entire mutagenicity. Thus, it is presumed that tobacco, tar and charred portions of meat and fish contain mutagenic substances other than B(a)P Benz(a)pyrene. Accordingly, recent studies of various substances have determined mutagenic substances are produced from many sources of protein or protein-derived substances when heated.

Although the Ames test is generally recognized as being effective for detecting compounds having mutagenic activity, there is a need for a procedure for isolating and identifying specific substances for testing by the Ames assay. For example, an organic material, such as macromolecular compounds or derivatives thereof, may be subjected to the procedure in accordance with the present invention to produce an identified substance which may then be subjected to the Ames test. Whereas in the past it was difficult to identify with certainty what particular component of the material, for example char-broiled steak, was responsible for mutagenic activity, the present invention provides a procedure whereby components of heat-decomposed materials may be separated, identified and tested for such activity.

Tars obtained by heating various amino acids possess various levels of mutagenic activity. In view of the above, an active substance in the tars of triptophan:

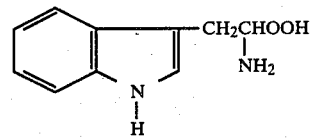

having the highest mutagenic activity was purified therefrom.

In accordance with the present invention, 330 grams of tryptophan were heated to obtain 205 grams of tar which were collected and purified to obtain two types of crystals, i.e. Trp-p-1 having the formula of:

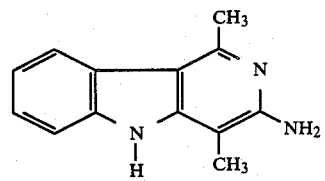

and Trp-p-2 having the formula:

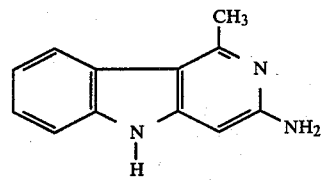

by 5 mg and 10 mg, respectively.

First, 330 grams of DL-tryptophan are charged in a flask. The flask is then heated with a gas burner to burn the DL-tryptophan, followed by cooling in ice to obtain approximately 205 grams of tar.

After an extraction with ether, the ether extract which corresponds to the basic fraction of the extraction is evaporated. The residue is then dissolved in ethyl acetate which is subjected to silica gel column chromatography. The column is eluted with 30% methanol in ethyl acetate and each fraction is measured for mutagenic activity.

The fractions showing mutagenic activity, which exhibits a single peak, is further subjected to alumina column chromatography ($Al_2O_3$). As before, the column is eluted with 30% methanol dissolved in ethyl acetate and each fraction is measured for mutagenic activity.

The fraction shown mutagenic activity are pooled and loaded to a CM-Sephadex C-25 column. The column is eluted with methanol and 2N acetic acid (3:1, v/v). Each fraction is then measured for mutagenic activity, and a single peak was found.

The fraction containing mutagenic activity is then loaded to a Sephadex LH-20 column and eluted with methanol. Two peaks were obtained, representing high mutagenic activity.

The eluant containing the first peak is then subjected to acetate salt crystallization, followed by NMR and spectrophotometric analysis, which revealed the material therein to be Trp-p-1, as shown below:

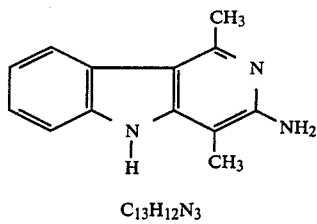

$C_{13}H_{12}N_3$

The eluant containing the second peak is then purified by CM-Sephadex chromatography, crystallized and also subjected to NMR and spectrophotometric analysis, which reveals the material therein to be Trp-p-2, as shown below:

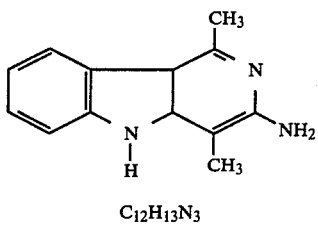

$C_{12}H_{13}N_3$

After having obtained crystals or other isolated forms of identified substances suspected of having mutagenic activity, these substances may be tested using the Ames assay method to make such a determination. For purposes of the example set forth herein, Lysosome, Histon, DNA and, RNA, as well as Starch and Vegetable oil are heat treated and processed in accordance with the isolation technique described above before being subjected to an Ames assay as follows:

The mutagenic activity for the heat decomposition product of the foregoing macromolecular vital compounds is tabulated below:

|  | TA 98 | | TA 100 | |
| --- | --- | --- | --- | --- |
|  | +S - 9mix | −S - 9mix | +S - 9mix | −S - 9mix |
| Lysosome | 8311 | 0 | 2319 | 0 |
| Histon | 5012 | 0 | 1311 | 0 |
| DNA | 278 | 0 | 170 | 0 |
| RNA | 83 | 0 | 0 | 0 |
| Starch | 0 | 0 | 70 | 338 |
| Vegetable oil | 0 | 0 | 85 | 0 |

No. of Mutagenic Colonies-mg., Tar-plate not containing colonies of natural

As used herein, TA-98 and TA-100 are those strains of Salmonella used as the primary screening for the search for mutagenic substances by the Ames method. It should also be noted that TA-98 is occasionally used in conjunction with PKM-101, which is a chemical resistant factor. In such cases, i.e. TA-98+PKM-101, the identification TA-1535 and TA-1538 is used to identify the strains.

A very important aspect of the present invention is the procedure whereby the vegetable fibers exhibiting the capability to adsorb mutagenic substances are separated from the vegetable and processed into a dehydrated particulate material. It has been discovered that the fibers of vegetables, and particularly those members of the group consisting of cabbage, radish, bamboo sprout, carrot, pimiento, spinach, soybean malt, and preferably asparagus, exhibit high mutagen adsorbability. It is believed, that if dehydrated fibrous vegetable particles made in accordance with the present invention are ingested together with foodstuffs containing mutagenic substances, the mutagens will be adsorbed by the fiber material, rather being digested, and will pass through and be excreted from the digestive track.

Although many fibrous vegetables may be processed in accordance with the present invention, such as those previously mentioned, the process of the present invention will be described herein using asparagus as the raw material source. The asparagus is first cleaned in preparation for subsequent processing. Although the entire stock may be used as the source of fibers, it is more economical to use the end-portions trimmed off the stalk which would otherwise be disgarded in preparation for subsequent processing into a commercial asparagus product. The asparagus stalk trimmings are subjected to a procedure where the fibers of the asparagus are separated from each other. It has been found particularly suitable to first boil the asparagus stalk trimmings in water followed by rinsing and washing with water to separate the asparagus into individual fibers which are dewatered and dried. The dehydrated fibers may then be reduced in size to a particulate form which is preferable powder, granules, or agglomerates of powder and/or granules.

Although any conventional dehydration expedient may be used to dehydrate the fiberous material in accordance with the present invention, it is preferred to puree the separated fibers into a slurry which may then be co-dried with carrier materials using conventional spray-drying techniques. A number of fruit and vegetable materials can be used as a carrier for the asparagus powder, with starch and fruit powder, such as pumpkin and plum being preferred.

Alternatively, the asparagus fibers may be separately dehydrated using conventional techniques, reduced to particulate form and dry-blended with such carrier materials.

Optionally, the slurry of asparagus fibers may be co-dried with one or more of other vegetable materials exhibiting mutagen-adsorbability.

Subsequently, dehydrated, fiber-rich vegetable products made in accordance with the present invention may be mixed with other foodstuffs and seasoned to improve their organoleptic characteristics for consumption.

Fiber-rich vegetables made in accordance with the present invention from cabbage, radish, bamboo sprout, onion, carrot, pimiento, spinach, soy bean malt, and asparagus as well as isolated cellulose were tested to determine mutagen adsorbability of Trp-p-1 and Trp-p-2 crystals produced in accordance with the procedure discussed above, by the following mutagen adsorption test:

The mutagen adsorbability of edible plant fibers was determined by utilizing the results obtained as above.

First, the vegetable fibers are taken up in an equal volume of water and boiled at 100° C. for two hours. After draining, the remaining material is subjected to a pressure of 1.3 kg/cm², and then dried at 40° C. for twelve hours. After drying, the material is pulverized to eliminate coarse fibers from the vegetable.

Mutagenicity assay
Preparation of pyrolysis products

Mutagens (Trp-p-1, Trp-p-2) were dissolved into dimethylsulfoxide (DMSD) at a concentration of 0.1–3 μg/ml.

The vegetable fibers prepared as above were immersed into the mutagen solution, which was subjected as the control.

First, 300 microliters are taken from the mutagen solution with immersed vegetable fibers, and added to 3 ml of soft agar at a temperature of 45° C. (Difco agar 0.5%, NaCl 0.6%). Next, 0.1 ml of TA 98 bacterial culture is added to the soft agar, followed by 0.3 ml of S-9 mix. The resulting mixture is streaked on a culture plate (1% Difco liquid broth, 0.1 microgram/ml biotin), and incubated for two days at 37° C. After incubation, the colonies are counted.

| Adsorption of Trp-p-1 and Trp-p-2 with Vegetable Fibers | | | | |
|---|---|---|---|---|
| | Trp-p-1 | | Trp-p-2 | |
| vegetable or the like for preparing fibers | Avg. No. of colonies* | Adsorbability (%) | Avg. No. of colonies | Adsorbability (%) |
| only mutagen (no addition) | 435 | 10 | 280 | 0 |
| +cabbage | 45 | 89.7 | 30 | 89.3 |
| +radish | 68 | 84.4 | 53 | 81.1 |
| +bamboo sprout | 52 | 88.0 | 55 | 80.4 |
| +onion | 76 | 82.5 | 63 | 77.5 |
| +carrot | 57 | 86.9 | 56 | 80.0 |
| +pimiento | 52 | 88.0 | 27 | 90.4 |
| +spinach | 46 | 89.4 | 32 | 88.6 |
| +soybean malt | 24 | 94.5 | 13 | 95.4 |
| +cellulose | 166 | 38.1 | 193 | 31.1 |
| +asparagus | less than 22 | more than 95 | 21 | 87.0 |

*his + in the case of introducing mutagen (only TA98 + S9-mix) - colony number 31

The foregoing examples have been presented to show that the fiber-rich edible vegetable materials produced in accordance with the present invention adsorb mutagen. Thus, it is believed that the occurance of cancer can be minimized by ingesting the product of the present invention as a food supplement taken in conjunction with other foods. Inasmuch as the natural vegetable materials from which the fiber-rich product of the present invention is processed normally contains 80–90% water, whereas the product of the present invention is an essentially dry powder, only a relatively small amount of product need be incorporated with other foodstuffs to derive the benefits of the present invention.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An ingestible product comprising dehydrated fiber-rich asparagus material in a form selected from the group consisting of powder, granules, agglomerates of powder, agglomerates of granules and agglomerates of powder and granules capable of adsorbing mutagen produced by a process consisting essentially of:
   separating fibers from asparagus;
   boiling said fibers;
   washing said fibers with water;
   dewatering said fibers; and
   dehydrating said fibers and
   forming dehydrated, fiber-rich asparagus material in paid particulate form.

2. The product of claim 1, wherein said process further consists essentially of including a carrier with said particulate form of dehydrated fiber-rich asparagus material.

3. The product of claim 2, wherein said carrier is selected is a member selected from the group consisting of dehydrated fruit and vegetable particulate material.

4. The product of claim 3, wherein said dehydrated fruit particulate material is a fruit powder is selected from the group consisting of pumpkin and plum.

5. A method for adsorbing mutagen present in foodstuff comprising:
   incorporating an amount of dehydrated fiber-rich asparagus material in a form selected from a group consisting of powder, granules, agglomerates of powder, agglomerates of granules, and agglomerates of powder and granules capable of adsorbing mutagen with a foodstuff.

6. A method for producing a powder capable of adsorbing mutagen consisting essentially of:
   separating fibers from asparagus;
   boiling said fibers;
   washing said fibers with water;
   dewatering said fibers; and
   dehydrating said fibers and forming dehydrated, fiber-rich asparagus material in particulate form selected from the group consisting of powder, granules, agglomerates of powder, agglomerates of granules, and agglomerates of powder and granules capable of adsorbing mutagen.

7. A method in accordance with claim 6, wherein said dehydrating is performed by co-drying said asparagus fibers with carrier materials.

8. A method in accordance with claim 6, further comprising dry-blending said dehydrated fiber-rich asparagus material with carrier materials.

9. A method in accordance with claim 8, wherein said carrier material is selected from a group consisting of dehydrated fruit and vegetable particulate materials.

* * * * *